United States Patent [19]

Mason et al.

[11] 4,181,134
[45] Jan. 1, 1980

[54] CARDIOTACHOMETER

[76] Inventors: Richard C. Mason, 19 Goodale Cir., New Brunswick, N.J. 08901; John D. Petronis, 93 Long Hill Rd., Little Falls, N.J. 07424

[21] Appl. No.: 835,478

[22] Filed: Sep. 21, 1977

[51] Int. Cl.$^2$ .............................................. A61B 5/02
[52] U.S. Cl. .................................. 128/689; 128/690; 128/706
[58] Field of Search ............... 128/2.05 P, 2.05 T, 128/2.06 F, 2.06 A, 2.06 B, 2.06 G, 2.06 R; 307/229, 230, 236; 340/347 NT; 324/780; 328/127, 129

[56] References Cited

U.S. PATENT DOCUMENTS

| | | | |
|---|---|---|---|
| 3,602,222 | 8/1971 | Herndon | 128/2.06 F |
| 3,633,569 | 1/1972 | Brayshaw et al. | 128/2.06 A |
| 3,701,142 | 10/1972 | Cannara | 340/347 NT |
| 3,734,086 | 5/1973 | Phelps, Sr. | 128/2.06 R |
| 3,802,698 | 4/1974 | Burian et al. | 272/57 R |
| 3,870,034 | 3/1975 | James | 128/2.1 Z |
| 3,893,449 | 7/1975 | Lee et al. | 128/2 V |
| 3,908,636 | 9/1975 | Page | 128/2.05 T |
| 3,910,260 | 10/1975 | Sarnoff et al. | 128/2.06 R |
| 3,937,004 | 2/1976 | Natori et al. | 58/152 B |
| 3,940,742 | 2/1976 | Hudspeth et al. | 340/172.5 |
| 3,955,355 | 5/1976 | Luce | 58/50 R |
| 3,985,121 | 10/1976 | Hellenbrand | 128/2 K |
| 4,017,766 | 4/1977 | Vercellotti et al. | 361/83 |
| 4,022,192 | 5/1977 | Laukien | 128/2.06 F |
| 4,090,504 | 5/1978 | Nathan | 128/2.05 R |

OTHER PUBLICATIONS

Advertisement entitled "Exersentry"; Manufacturer is Respironics Inc., Middle Ave. at 3rd St., Wilmerding, Pa. 15148.
New York Times, "Patents: An Electronic System for Intravenous-Infusion Control", Aug. 6, 1977.
Runner's World, "Good News", Jul., 1977.
Advertisement entitled "Introducing the Basic Cardiac Diagnostic Instrument of the 70's.", Medcraft, Inc., Skippack, Pa.
Advertisement entitled "Dyna-Gram Recorder Model 5000", Cardio-Dynamics Laboratories, Inc., 12401 W. Olympic Blvd., L.A., Calif. 90064.
Advertisement entitled, "Phipps & Bird Bio-Monitor", Phipps & Bird, Inc., P.O. Box 2732A, Richmond, Va., Bulletin #7092-910-75.
Advertisement entitled "2D16 Pulsemeter", Medical Systems Corp., 230 Middle Neck Rd., Great Neck, N.Y. 11021.
Advertisement entitled "FJC-7110 Mini-ECG Series", manufactured by Fukuda Denshi Ltd.
Advertisement entitled "Heart Patient Monitor-Model (ECC1-50 B", Fukuda Denshi Co., Ltd.
Advertisement entitled "One Pound Cassette Recorder", Clinical Data, Inc., 358 Chestnut Hill Ave., Box 430, Brookline, Mass.
Electronics Magazine, "Consumer", p. 32, Apr. 28, 1977.
IEEE Transactions on Biomedical Engineering, "Triboelectric Interference in the ECG", by D. H. Gordon, BME-22-#3, pp. 252-255.

*Primary Examiner*—Robert W. Michell
*Assistant Examiner*—Jeffrey W. Tayon
*Attorney, Agent, or Firm*—Richard C. Woodbridge

[57] ABSTRACT

A cardiotachometer includes features which reliably filter out interfering background signals and provide for relatively low power consumption. A differential amplifier is connected to a three electrode input so as to effectively reduce common mode errors. The output of the differential amplifier is connected to an automatic polarity selecting circuit and an automatic gain control amplifier so as to make the unit as independent as possible from user adjustment. The device includes an eight bear counter for producing a single output pulse for every eight input pulses. The output of the eight beat counter is connected to a dual slope analog-to-digital converter for developing a display which is directly related to the average heart rate over a eight beat period and inversely related to the voltage applied to the circuit. A low power liquid crystal display is connected to the output of the dual slope circuit.

15 Claims, 7 Drawing Figures

CARDIOTACHOMETER

BACKGROUND OF THE INVENTION

1. Field of the Invention

This invention relates to a compact cardiotachometer having high reliability and relatively low power consumption.

2. Description of the Prior Art

The patent literature discloses many devices for monitoring the physical parameters of the human body. For example, Natori et al, U.S. Pat. No. 3,937,004, discloses an electronic device adapted to be worn on the wrist of a user. The device includes sensors responsive to conditions such as temperature or blood pressure. The output of the device is preferably indicated in an associated display mechanism.

U.S. Pat. No. 3,802,698 to Burian et al discloses an exercise measuring system which includes pick-up electrodes strapped to the patient's chest. The pulse rate of the person is displayed by an electronic indicating device.

James, U.S. Pat. No. 3,870,034 is notable for the disclosure therein of another monitoring device which may be worn on the wrist.

Sarnoff et al, U.S. Pat. No. 3,910,260 is of interest for the disclosure of a portable battery-operated device having a pair of electrodes positioned so as to provide signals indicative of the heart beat condition.

Lee et al, U.S. Pat. No. 3,893,449, Hellenbrand, U.S. Pat. No. 3,985,121 and Page, U.S. Pat. No. 3,908,636 are all exemplary of various types of portable electronic devices for measuring the physical condition of a human.

The patent literature also discloses that wrist mounted electronic units are known in the prior art. See for example, Luce, U.S. Pat. No. 3,955,355 which discloses a wrist mounted electronic unit adapted for digital computing and displaying information.

An article which is believed to have appeared in the Saturday, Aug. 6, 1977 issue of the NEW YORK TIMES, describes a pulse monitor that can be used by joggers, tennis players, and other exercisers. The device is apparently disclosed in U.S. Pat. No. 4,038,976 to Frank M. Hardy and Theodore W. Coffey. The instrument is described as sensing or detecting pulses by sound and transmitting them to a visual or audible display, or both. If the pulse is indicated visually, a light gets brighter as the pulse grows stronger and gets dimmer if it grows weaker. The instrument can also be operated digitally, so that the pulse rate is indicated in figures. The indicator of the device is described as being fastened to the wrist of the user.

Another article of interest appeared in the July 1977 issue of RUNNER'S WORLD. That article made the following disclosure:

"Harold S. Geneen, Chairman and Chief Executive of the International Telephone and Telegraph Corp. (ITT), has been granted a patent on 'wrist-watch' pulse-rate indicator. Besides its usefulness for joggers who would like to know if they're exceeding the safe limits of cariovascular activity without having to stop and take their pulse, the indicator is helpful during sedentary situations for people whose emotions tend to boost their heart rates. The device displays the wearer's heart rate in three forms: digital, color (green for rest, amber for safe exercise level, and red for danger) and by an audible beep in conjunction with the red light.

How soon ITT will produce the pulse-rate indicator is still under consideration."

There are a variety of large scale cardiac diagnostic instruments available on the market all of which can be used to determine heart rate. For example, Medcraft, Inc., Skippack, Pa. 19474 manufactures an item known as the CDC 70 System. The CDC 70 system is a table model cardiac diagnostic center including a Holter Monitor/Scanner stress test monitor, resting ECG sensor, patient bedside monitor, telemetry monitor and a computer tie-in device. A similar device appears to be in STAR-100 Stress Test and Rehabilitation Unit manufactured by the same corporation.

Cardio-Dynamics Laboratories, Inc., 12401 West Olympic Boulevard, Los Angeles, California 90064 produces a system of instruments including a Dyna-Gram ® Recorder Model 5000 which is attached to a heart patient and designed to keep a continual 24 hour record of the patient's ECG. signals. The recorder is approximately 2 lbs. in weight and the information is stored on a standard cassette. The cassette may be subsequently removed and analyzed on a Dyna-Gram ® Scanner Model 6001 which can be used to process the signal stored on the recorder.

Phipps and Bird, Inc., P.O. Box 27324, 8741 Landmark Road, Richmond, Virginia 23261 produce a Bio-Monitor for basic bioelectric experiments. The Bio-Monitor is a low cost, relatively uncomplicated instrument. The Phipps and Bird, Inc. Catalog No. 57 states that ". . . the Bio-Monitor performs as a versatile, reliable student station for work with most verterbrates, including man. Experiments suggested in the manual include: determining mean heart beat, heart rate differences by sex and height, effects of rapid breathing and exercises. Basically, the Bio-Monitor is a millivolt amplifier that provides both visual and audible response (flashing light and beep sound). It operates on transistor radio-type batteries, and the complete kit contains everything ready for student use."

Medical Systems Corp., 230 Middle Neck Road, Great Neck, New York, 11021 produces a portable pulse rate indicating meter Model 2D16 which is small in size and may be used in emergency situations. In operation a light from a tiny lamp in the pickup is defused through the finger tips to illuminate a cadmium sulphide photo-cell. The light is interrupted by the pulsatile blood flow, causing the electrical resistance of the photo-cell to vary with each pulsation. Transistorized amplifier circuits detect the resistance variation and compute the number of beats per minute which is indicated on a meter scale. Additional transistor circuits amplify the photo-cell signal to operate a speaker. In the ear lobe pick-up mode, a light source passes through the ear lobe tissue and reaches, with pulpatory signals the photo-cell. The Medical Systems Corporation also supplies several other instruments including the FJC-7110 "Mini-ECG Series" manufactured by Fukuda Denshi, Ltd. The FJC-7110 Series includes a battery operated, portable ECG and related power supply and accessory equipment. Fukuda Denshi, Ltd., also produces a heart beat patient monitor Model ECU-50B which may be mounted on a stand and wheeled into position in an operating room or in the convalescent section of a hospital. Similarly, Fukuda-Denshi, Ltd. also manufactures an electrocardiograph, Model FD-13 which monitors ECG activity and preserves the information on a strip chart.

Clinical Data, Inc., 358 Chestnut Hill Avenue, Box 430, Brookline, Massachusetts, 02146 produces a one pound battery operated cassette recorder which permits up to 24 hours of continuous ambulatory ECG recording. Apparently information is gathered and stored on two channels in the FM mode.

The Apr. 28, 1977 edition of ELECTRONICS Magazine describes a combination watch and pulse-rate monitor recently manufactured by Time Computer, Inc., Lancaster, Penna. The monitor reads the pulse rate with an infrared sensing unit that detects blood surges from the capillaries of a finger and subsequently transmits the information to a micro-computer. The processed information may be set forth on a visual display.

Respironics, Inc., Middle Avenue at Third Street, Wilmerding, Penna. 15148 produces a heart rate monitor sold under the mark EXERSENTRY. The Respironics device is adapted especially for monitoring heart conditions during prescribed exercise programs. The EXERXENTRY computes the heart rate electronically and incorporates a liquid crystal display to continuously indicate the heart rate in beats per minute. The digital read out can display heart beats from 40 BPM to over 210 BPM. The EXERSENTRY also includes the following features: a light emitting diode which blinks to show each heart beat; an automatic sensitivity adjustment to automatically adapt to each user's heart beat; an impact resistant plastic case and soft, plastic ECG pick-up electrodes.

Finally, the May 1975 edition of the IEEE Transactions on Biomedical Engineering included an article entitled "Triboelectric Interference in the ECG". The article was authored by David H. Gordon and appeared on pages 252-255. It addresses some of the basic problems facing the manufacturers and users of ECG Monitors. The article also includes an interesting background description of the types of problems faced by the inventors of the device described herein. However, the inventors of the present invention encountered several additional problems other than those described in the Gordon article and were able to successfully overcome them.

SUMMARY OF THE INVENTION

Briefly described, the invention comprises a lightweight, low power, portable cardiotachometer. The electronic package comprises three basic different sections. The first basic section provides the initial signal processing and includes a differential amplifier, a bandpass filter, an automatic polarity selector, and an AGC amplifier. The second basic section performs the function of detecting the QRS heart beat complex. The second basic section includes a threshold detector, a monostable circuit, an eight beat counter and a timing pulse generator. The third, and last basic section of the electronic package performs the function of taking the time reciprocal of the period of the pulses generated by the second basic section. The third basic section includes a ramp generator, a sample-and-hold circuit, and a ratiometric analog-to-digital converter. The output of the electronic package is fed to a low power consumming, liquid crystal display. A three electrode system is employed to pick-up the very weak ECG signals and feed them to the inputs of the differential amplifier.

These and other features of the invention will be more fully understood by referring to the following drawings and the detailed description of the invention.

DETAILED DESCRIPTION OF THE INVENTION

During the course of this description like numbers will be used to indicate like elements on the different figures which illustrate the invention.

In order to understand the invention it is desirable to first examine the general problems associated with the analysis of ECG signals. The typical electrocardiogram signal has an amplitude between tenths of a millivolt and several millivolts. In addition, the fourier spectrum of an ECG signal extends effectively up to the thirtieth harmonic of the fundamental frequency component. Therefore an individual with a heart rate of 120 beats per minute, a condition which is likely to occur during exercise, might exhibit an ECG signal that contains frequency components up to 60 hertz.

Analysis of the ECG signal is difficult because of interfering signals generated by sources surrounding the user or by processes related to the active movement of the subject. Generally, the interfering signals can be placed in two categories, to wit: signals introduced in the common mode and signals introduced in the differential mode.

Signals that are introduced in a common mode manner all follow the same electrical pathway. The pathway can be described in the following manner. The typical undesired signal is capacitively coupled to the body. The body is a relatively good conductor which generally exhibits a resistance in the order of hundreds of ohms. The undesired signal is frequently an undesired current which flows through the body and then from there through the relatively high impedance which is associated with the contact of the pick-up electrodes to the surface of the body. This impedance may be of the order of anywhere from several thousand ohms for a properly prepared electrode to greater than 100,000 ohms for an improperly prepared electrode. The undesired current, therefore, flows through the body, through the relatively high impedance of the electrodes, and then from there back to earth ground by means of stray capicitance.

The two most prevelant forms of common mode interference are sixty hertz interference and interference introduced by the movement of charges generated by an individual wearing an insulating material, such as a neoprene sole or the rubber sole on a sneaker. In the case of 60 hertz, the capacitive coupling between the body and surrounding 60 hertz wiring causes an undesired current to flow through the body, through the relatively large electrode impedances, and back to earth ground. The second kind of external interference is caused by the generation or discharge of static electricity. The charge flow due to this phenomenon is called triboelectric noise. A very useful article entitled "Triboelectric Interference in the ECG" was written by David H. Gordon and appeared in the May 1975 issue of the *IEEE Transactions on Biomedical Engineering*. This is the article cited supra in the "Description of the Prior Art" section of this specification. In the case of a current generated by wearing an insulating material, the motion of the user causes the current to be generated because a potential difference usually exists between the body and the earth ground. When the ECG user moves he changes his capacitance with respect to earth ground. The change in capacitance causes current to flow through the body, through the electrodes, and back to earth ground thereby generating a sizable common mode interference signal. The inventors of the device described herein are believed to be among the first to recognize the serious interference problems caused by wearing of insulating material. This problem is especially severe in the case of athletes who wear a rubber-type sole on their sneakers.

Differential interfering signals primarily arise from two sources.

The first source is the signal which is generated by the movement of an electrode with respect to the user's body. This may happen, for example, when an individual disturbs the metal of a pick-up electrode which has been placed in position on the body of a user and held in electrical contact therewith by means of an electrode gel. Similarly, the same type of signal may be generated when the gel itself is disturbed. Many of the differential interfering signals which are generated by the movement of the electrode with respect to the body fall into the same frequency range as the ECG Fourier components.

The second main source of interfering signals introduced in a differential manner are those signals which arise from muscle potentials. These invariably occur when muscles contract and are the result of ion shifts within and between muscle cells and their environment. The Fourier spectrum of signals generated by muscle potentials extend from approximately 35 hertz to several Kilohertz. Accordingly, myoelectric signals may interfere with the ECG signals. It has been found that the ECG potential is a function of the position of the electrodes and may vary from individual to individual given the same electrode arrangement. It is not desirable for a user of a portable ECG instrument to adjust or readjust the placement of the electrodes. Accordingly, the problem of muscle potentials had to be taken into account in the development of the invention described.

In addition to the foregoing, it was also desirable that the ultimate device be easy to wear, be small in size and have a relatively low power consumption.

In order to partially solve some of the problems set forth above, the following approach has been taken. It was found that interfering common mode signals could be reduced in magnitude by two techniques. One technique was by choosing to use a system that includes an electrode gel which decreased the impedance of the electrode and therefore reduced the magnitude of the interfering signals. According to a second technique, residual interfering common mode signal were eliminated by using a differential amplifier as the first stage of the electronic package of the cardiotachometer.

Similarly, interfering differential signals, can be reduced in magnitude by two other techniques. First of all, interfering signals arising from electrode movement can be reduced in magnitude by properly selecting the material that is used for the electrode and by carefully paying attention to the means by which the electrode is held in contact with the body. Second of all, differential signals arising from muscle potentials can be greatly reduced in magnitude by employing appropriate electronic filtering techniques. The ECG Fourier spectrum of possible potential signals may extend out to the thirtieth harmonic. However, the most important part of the heart beat signal is the so-called QRS complex which has a spike-like shape. Therefore by severely limiting the bandwidth of the electronic system it is possible to pass just the QRS spike portion and reject the myoelectric signals. Accordingly, a band pass filter was included in the cardiotachometer circuit. The preferred characteristic of the band pass filter is approximately 10 to 30 hertz.

Figures 1, 2, 3:
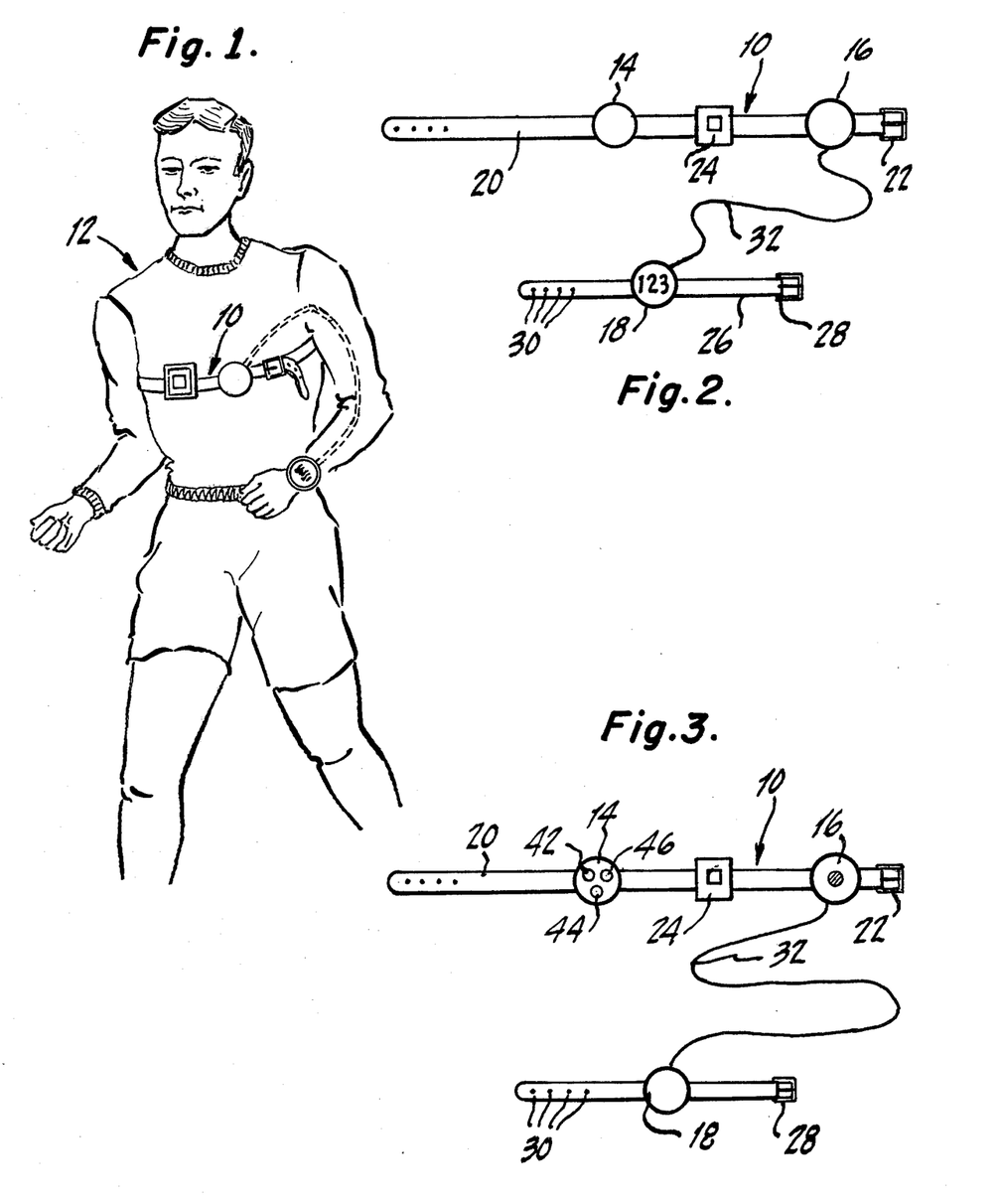
FIG. 1 illustrates the manner in which the cardiotachometer of the present invention is worn by a user.
FIG. 2 is a front view of some of the basic elements of the invention as mounted on a chest band.
FIG. 3 is a rear view of the elements illustrated in FIG. 2.

FIG. 1 illustrates the manner in which the cardiotachometer 10 of the present invention is strapped to the body of a user 12. The user 12 in this case might be a runner or any other individual engaged in moderately strenuous exercise. It will be appreciated, however, that the invention may be used on a wide variety of other individuals either in the active state or at rest.

FIGS. 2 and 3 illustrate in greater detail the manner in which the elements of the invention are physically associated with one another. It should be understood by those of ordinary skill in the art that the specific physical relationship of the elements as illustrated in FIGS. 1 through 3 do not form a critical part of the invention. FIGS. 1 through 3 are provided merely to provide a better general understanding of the purpose of the invention. It will be clear to those of ordinary skill in the art that various different physical arrangements might be just as acceptable.

The cardiotachometer 10 includes a set of pick-up electrodes 14, an electronic package 16 connected to the pick-up electrodes 14 and a digital display 18 connected to the output of the electronic package 16. Pick-up electrodes 14 and the electronic package 16 are mounted on chest strap 20. Chest strap 20 preferably includes at least one fastening buckle 22 and a tightness adjustment element 24. A display 18 is carried on a wrist band 26 similar to those used with wrist watches. Wrist band 26 includes a conventional buckle 28 and a plurality of buckle adjustment holes 30. A short length of wire 32 connects the display device 18 to the electronic package 16. FIG. 2 illustrates the cardiotachometer elements as seen from the front and FIG. 3 illustrates the same elements when viewed from the rear. The pick-up electrodes 14 may not be visible from the front as shown in FIG. 1. Typically, electrode package includes three electrodes 42, 44 and 46 as will be more fully understood with reference to the detailed description of the electronic package 16 in FIGS. 4 and 5A, 5B and 5C.

Figure 4:
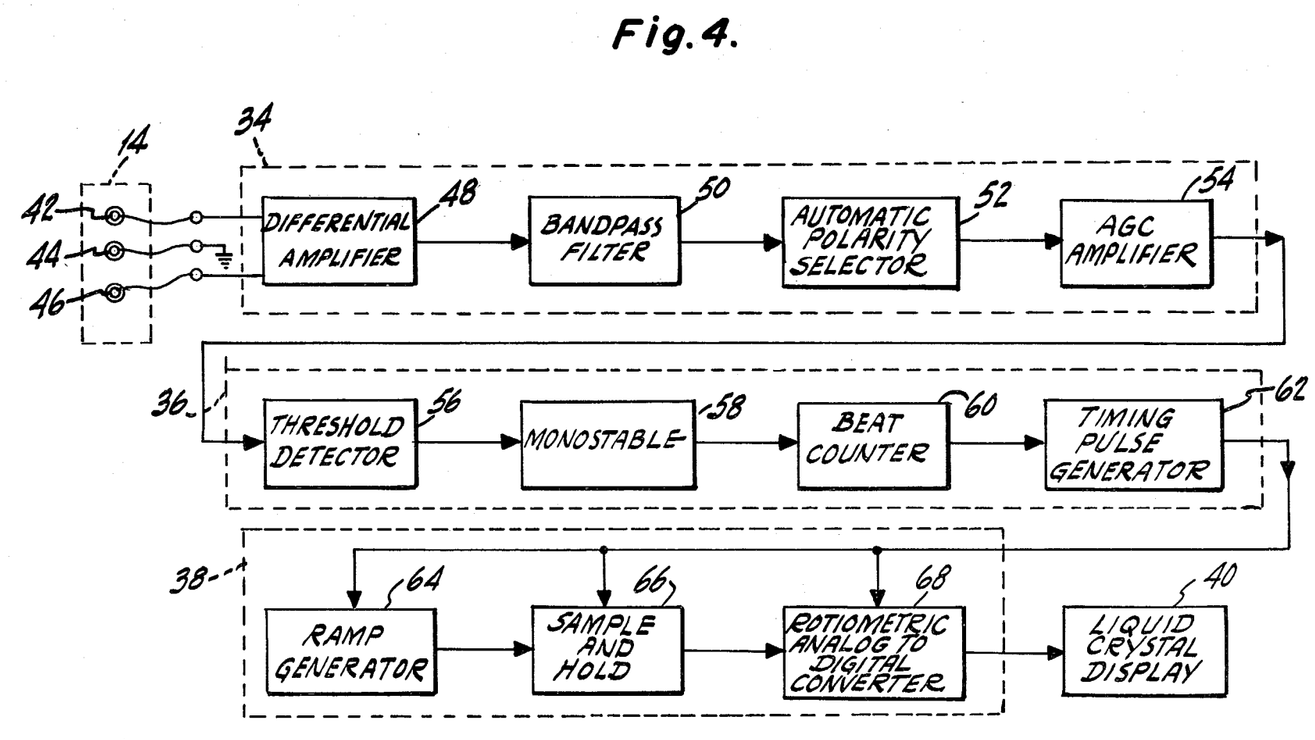
FIG. 4 is a block diagram of the basic electronic package of the cardiotachometer.

FIG. 4 is a block diagram of the basic elements of the invention. The block diagram comprises three different basic circuits, namely an initial signal processing circuit 34, a signal recognizing circuit 36 and a reciprocal generating circuit 38 which drives a liquid crystal display 40. The liquid crystal display 40 is incorporated in the watch-like housing 18 illustrated in FIGS. 1 through 3. The three basic circuits 34, 36 and 38 comprise the electronic package 16. Three pick-up electrodes 42, 44 and 46 are connected as inputs to the electronic package 16. Pick-ups 42 and 46 are respectively connected to the opposite inputs of differential amplifier 48 which comprises the first stage of the initial signal processing unit 34. The remaining pick-up electrode 44 is connected to earth ground.

The first signal processing section comprises differential amplifier 48, bandpass filter 50, automatic polarity selector 52 and automatic gain control (AGC) amplifier 54. The purpose of the first section is to provide the initial amplification and discrimination processes on the ECG signal.

The second section 36 performs the function of recognizing the QRS complex even though a small amount of background noise may still exist. The second section 36 includes a threshold detector 56 connected to the output AGC amplifier 54, a monostable circuit 58. an eight beat counter 60 and a timing pulse generator 62. The eight beat counter 60 produces one output for every eight inputs heartbeat signals received from monostable circuit 58. The output of the eight beat counter 60 is shaped by timing pulse generator 62 so as to prepare it for processing by the final section 38 of the electronic package 16.

The third, or final section 38, includes one of the more important aspects of the present invention. Its purpose is to measure the time that it takes for the eight beats to occur and then to take the reciprocal of this time interval so as to develop a heart rate indications which will appear on the liquid crystal display 40. The third section 38 includes a ramp generator 64, a sample and hold circuit 66 and a ratiometric analog-to-digital converter circuit 68. Circuits 64, 66 and 68 are commonly fed from the output control line of the timing pulse generator 62.

The signal flow through the block diagram illustrated in FIG. 4 is as follows. The signal first enters differential amplifier 48. At that location the signal is amplified and common mode interfering signals are rejected. The output of the differential amplifier 48 is fed into a band pass filter 50 which reduces the magnitude of many of the interfering signals that have been introduced into the input signal in the differential mode. The signal then proceeds to automatic polarity selector 52 and AGC amplifier 54. The purpose of those two elements is to make the cardiotachometer unit as independent of the electrode placement as possible. The signal entering the automatic polarity selector 52 may have either a positive going or negative going polarity associated with it depending upon the placement of electrodes 42. However, the output of the automatic polarity selector 52 is always a negative going QRS complex. The output of the automatic polarity selector 52 comprises the input of AGC amplifier 54. The function of the AGC amplifier 54 is to adjust the gain of the signals so that the output of stage 54 is always held at a constant amplitude level.

The output of AGC amplifier 54 forms the input of threshold detector 56. Threshold detector 56 will not pass any signal including the QRS complex until it reaches a certain predetermined voltage level. Therefore threshold detector 56 serves as a final filter to reduce any residual interfering signals that may be left over from the processing by the initial signal processing section 34. Hence, by employing a threshold detector having a threshold level which is greater than the normal background interfering signals, the QRS complex will be recognized and the background noise will be rejected (i.e. clipped). The relatively pure QRS signal is then fed from the threshold detector 56 into the input of a monostable circuit 58. The purpose of monostable circuit 58 is to produce square wave pulses having known fixed amplitudes and duration. It is desirable to have uniform signals as an input to subsequent circuitry so that the subsequent circuit stages can be reliably triggered. The output of the monostable circuit 58 is fed to the input of eight beat counter 60. The eight beat counter 60 will count eight incoming pulses from the monostable circuit 58 and produce a single output-pulse every time eight sequential input pulses have been counted. The output of the eight beat counter 60 feeds the input of timing pulse generator 62. Timing pulse generator 62 produces two pulses which are relatively narrow in time. Each of the two pulses is approximately 10 milliseconds long. The leading edge of the second pulse is coincident with the trailing edge of the first pulse. These pulses are used to control the third section 38 of the cardiotachometer.

The third and final sections 38 operates in the following manner. Ramp generator 64 is initially reset to ground (i.e. 0 volt). The output of the ramp generator 64 increases at a linear rate. Therefore, the amplitude of the output of ramp generator 64 is a direct function of time. Just prior to the ramp generator 64 being reset at the end of eight beats, the control pulses from timing generator 62 activate the sample and hold stage 66 so that the value of the ramp at the end of the eighth beat is held in the sample-and-hold circuit 66. Ramp generator 64 is then reset to zero. Next the control pulses are used to activate the ratio-metric analog-to-digital converter 68 which examines the value of the signal stored in sample and hold stage 66. Analog-to-digital converter 68 produces a display which is an inverse function of the input signal. The output of analog-to-digital converter 68 drives a liquid crystal display 40. A liquid crystal display 40 was chosen primarily because of its low power consumption characteristics. The following detailed description of the preferred embodiment of the circuit itself according to its best mode will be relatively easy to understand in view of the foregoing description of the block diagram of FIG. 4.

Figure 5A:
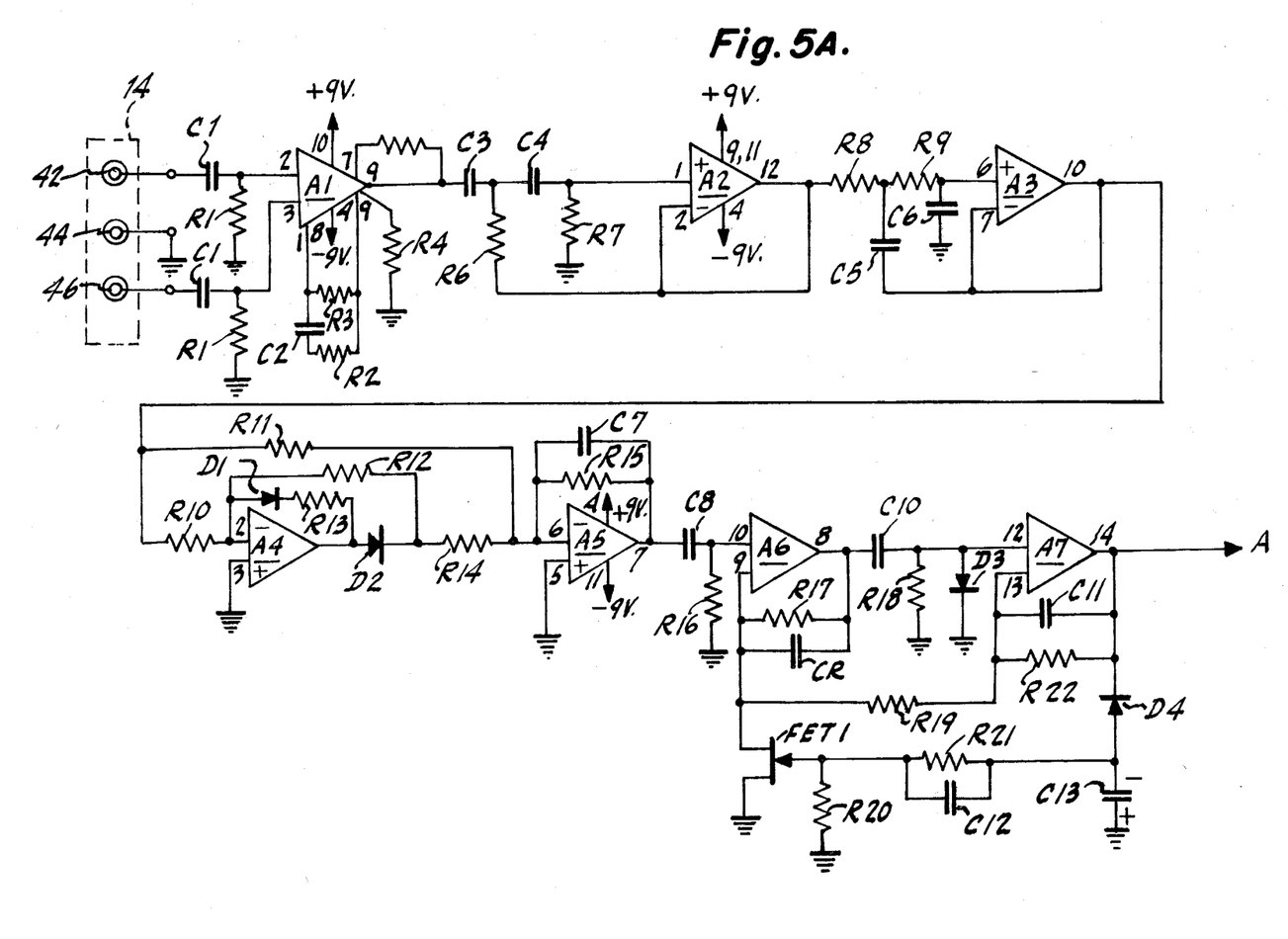
FIGS. 5A, 5B and 5C are detailed schematics illustrating the relationship of the specific elements which comprise the cardiotachometer electronic package illustrated in FIG. 4.
Figure 5B:
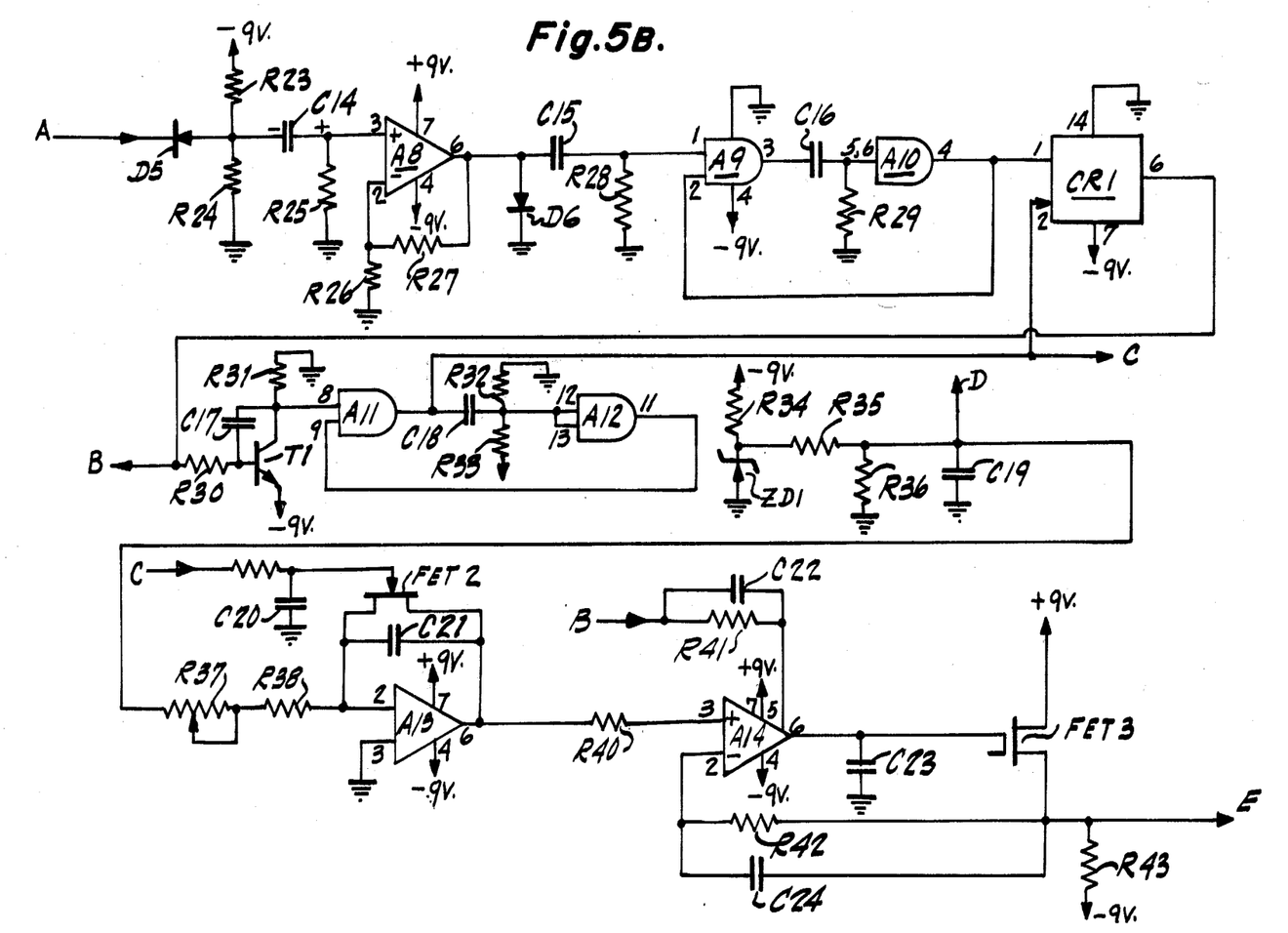
Figure 5C:
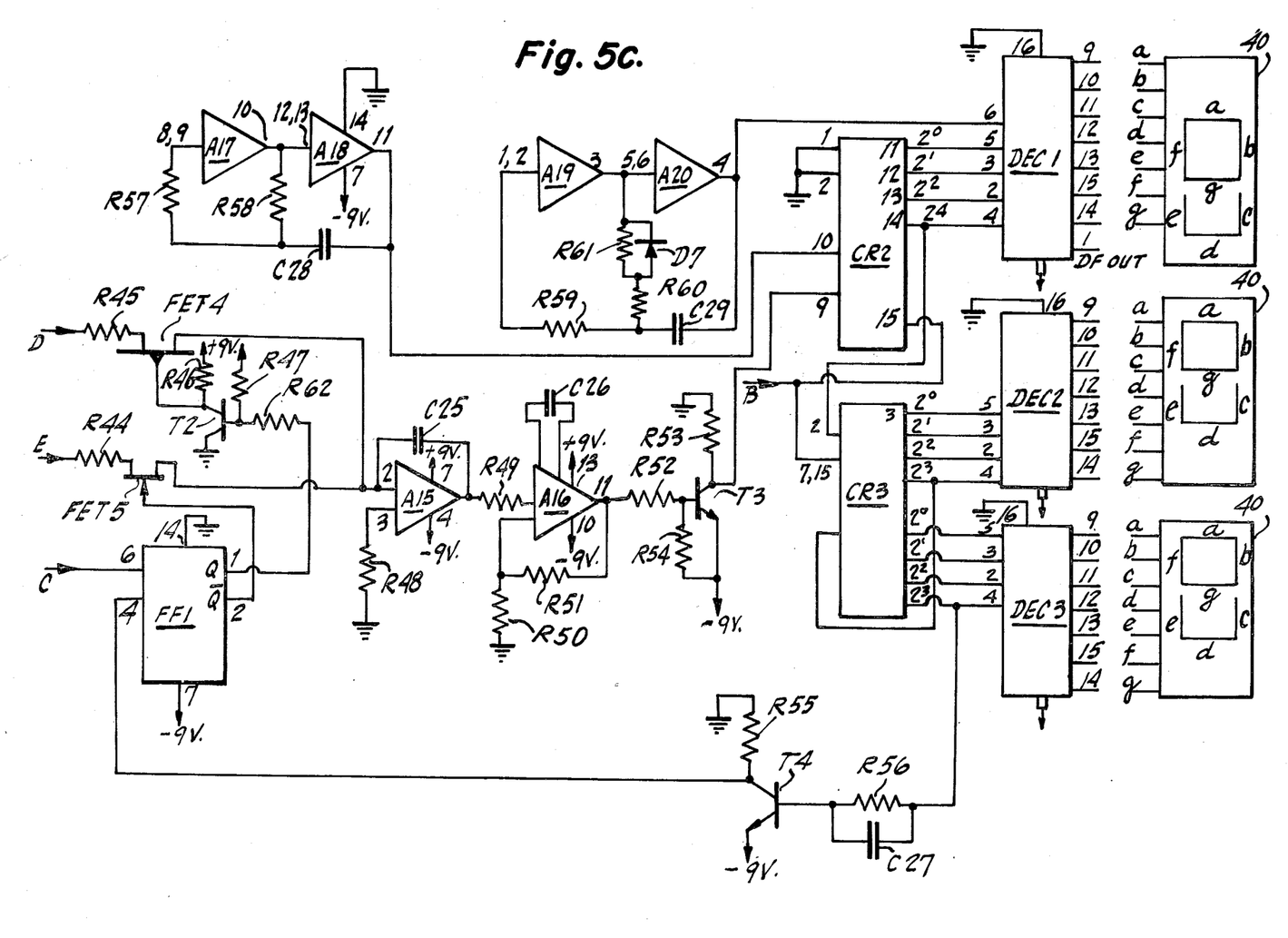

The schematic diagrams in FIGS. 5A, 5B and 5C describe in detail the manner in which the various different sub-elements of the electronic package 16 are connected together. Input electrodes 42, 44 and 46 are connected in the manner previously described with reference to FIG. 4 to the input of the circuit. Two of the electrodes, 42 and 46 are connected to the two inputs of differential amplifier A1. Differential amplifier A1 comprises a Burr-Brown 3660 J integrated circuit. One important feature of the differential amplifier A1 is its gain determining network which exists between pins 1 and 4 of the integrated circuit. The gain controlling network comprises a 100 K ohm resistor R3 in a parallel circuit with a 100 ohm resistor R2 in series with a 150 microfarad electrolytic capacitor C2. The characteristics of the gain determining network is such that the differential amplifier A1 exhibits unity gain at DC and the gain increases at a 6 db per octave rate with a break point being at approximately 8 hertz. Beyond that point, the gain is essentially constant and fixed at 1,000. Pick-up electrodes 42 and 46 are respectively coupled to input pins 2 and 3 of differential amplifier A1 through 1 microfarad coupling capacitors C1. Coupling capacitors C1 are connected to ground through 10 megohm resistors R1 respectively. A pair of 51 K ohm resistors R4 and R5 act as load resistors for the output stage of differential amplifiers circuit A1. Resistor R4 is connected between pin 9 and ground. Resistor R5 is connected between pin 7 and pin 9.

The output from the differential amplifier section 48 is coupled to band pass amplifier section 50 which comprises a cascaded high-pass filter network and a low-pass filter network. The band pass network 50 includes two amplifier sections A2 and A3 which are part of a single National Semiconductor 747 integrated circuit. The characteristics of the high-pass and low-pass filter sections are that they have a 12 db per octave roll-off and that they exhibit a unity gain within the flat portion of their characteristic curves.

The high-pass filter circuit includes the first half of the type 747 integrated circuit amplifier A2 and two series connected 0.15 microfarad capacitors C3 and C4 connecting pin 9 of amplifier A1 to pin 1 of amplifier A2. A first 110 K ohm resistor R7 connects pin 1 of amplifier A2 to ground. A second 110 K ohm resistor R6 connects the output pin 12 of amplifier A2 to the junction between capacitors C3 and C4. The cutoff frequency of the high pass filter section is approximately 10 hertz.

The output of the high-pass filter amplifier A2 is connected through a pair of series connected 33 K ohm resistors R8 and R9 to input pin 6 of amplifier A3. The output pin 10 of amplifier A3 is connected by a 0.15 microfarad capacitor C5 to the junction between input resistors R8 and R9. Pin 6 of amplifier A3 is connected to ground by another 0.15 microfarad capacitor C6. Amplifier A3 is the heart of the low-pass filter section and is incorporated in the other half of the type 747 integrated circuit. Output pin 10 of amplifier A3 is connected to input pin 7 of amplifier A3. In a similar manner the output pin 12 of amplifier A2 is connected to input pin 2 of amplifier A2. The upper cutoff frequency of the low pass filter section is approximately 35 hertz.

The output of the band pass filter network 50 is fed into the input of the automatic polarity circuit 52. The structure and function of the automatic polarity selector circuit 52 and its use in the context of a cardiotachometer is believed to be relatively unique. The automatic polarity selector circuit 52 functions in a manner similar to that of a full wave rectifier. It consists of two operational amplifiers which may be National Semiconductor type LM 324 integrated circuits. Automatic polarity selector 52 operates in the following manner.

The output of amplifier A3 is applied to the input of two 10 K ohm resistors R10 and R11. If the signal is positive going, then no output exists at the cathode of hot carrier diode D2 which is connected to pin 1 of amplifier A4. Therefore, diode D2 is non-conducting and becomes an open circuit. The 1 K ohm resistor R13 and hot carrier diode D1 which appears between pin 1 and 2 of amplifier A4 prevent the stage from saturating when a positive going signal is applied at the input. Accordingly, a positive going signal applied to pin 2 of amplifier A4 causes the circuit to become non-conducting, i.e. an open circuit. The following portions of the circuitry of the automatic polarity selector 52 are relevant for positive going signals. 10 K ohm resistor R11 connects pin 6 of amplifier A5 to the output pin 10 of amplifier A3. Pins 6 and 7 of amplifier A5 are connected by a parallel combination of a 0.47 microfarad capacitor C7 and a 10 K ohm resistor R15. The performance of components R11, R15, C7 and A5 is such that a positive going signal applied to the input of the automatic polarity selector 52 is inverted so that a negative going signal will appear at the output of pin 7 of amplifier A5.

When the input signal to the automatic polarity selector stage 52 is negative, then the circuit acts in the following manner. Amplifier A4 will act as an inverting unity gain amplifier so that the signal appearing at the junction of the hot carrier diode D2 located at pin 1 of amplifier A4 and the 4.7 K ohm resistor R14 is an inverted, positive going signal, whose amplitude is equal to that of the input signal. At the same time the negative going signal is also applied to the 10 K ohm resistor R11 that connects the output of amplifier A3 to the input pin 6 of amplifier A5. The action of elements R11, R14, R15 amd C7 in combination with amplifiers A4 and A5 is to form a circuit that performs both summation and inversion of the input signals with a different gain depending upon where the signal is applied. For example, a signal applied to resistor R11 will be inverted and will appear at output pin 7 of amplifier A5. Therefore, a negative going signal with an amplitude of 1 volt will appear as a positive going signal with an amplitude of 1 volt at the output of amplifier A5. However, the same signal (for the sake of this example, a 1 volt negative going signal) is inverted by amplifier A4 and is applied via resistor R14 to input pin 6 of amplifier A5. The positive going signal is then amplified and inverted with a gain of 2. Accordingly, the output of amplifier A5 consists of a positive going signal with a 1 volt amplitude summed with a negative going signal of 2 volt amplitude so the net result is a 1 volt negative going signal. Accordingly, the action of the circuit is such that for either a positive going signal or a negative going signal, the result at the output of amplifier A5 is always a negative going signal with a unity gain with respect to the input of the system.

The output from pin 7 of amplifier A5 is fed through a 50 microfarad coupling capacitor C8 to input pin 10 of amplifier A6. A 10 K ohm resistor R16 connects input terminal 10 to ground. Automatic gain control amplifier 54 essentially consists of two cascaded amplifiers A6 and A7 inter-connected by a series of impedance elements. Amplifiers A4, A5, A6, and A7 are all part of a single National Semiconductor type LM 324 integrated circuit. Output pin 8 of amplifier A6 is connected back to input pin 10 of amplifier A6 by a parallel combination of a 0.05 microfarad capacitor C9 and a 68 K ohm resistor R17. In a similar manner, output pin 14 of amplifier A7 is connected to input pin 13 of amplifier A7 by a parallel combination of a 0.005 microfarad capacitor C11 and a 1 megohm resistor R22. Output pin 8 of amplifier A6 is connected to input pin 12 of amplifier A7 through a 1 microfarad coupling capacitor C10. Pin 12 is also connected to ground by a 220 K ohm resistor R18 and a hot carrier diode D3. A 68 K ohm resistor R19 connects input pin 9 of amplifier A6 with input pin 13 of amplifier A7. The gain feedback control circuit from pin 14 of amplifier A7 to pin 9 of amplifier A6 includes a hot carrier diode D4, capacitor C13, then to the parallel combination of a 150 K ohm resistor R21 and a 0.1 microfarad capacitor C12 which in turn is connected to the gate of FET 1. Pin 9 of amplifier A6 is connected to ground through the source and drain of FET 1 which may be a Motorol type HEP 801. The gate of FET 1 is connected to ground through a 47 K ohm resistor R20.

AGC circuit 54 operates in the following manner. As the output of the AGC amplifier 54 increases in amplitude, its peak value is detected by means of hot carrier diode D4 and electrolytic capacitor C13. The result is a DC potential which is approximately equal to the peak value of the output signal. The DC potential is applied via the voltage divider consisting of resistor R21 and R20 as an input to the gate of FET 1. This in turn causes FET 1 to be driven further towards its cutoff region and, therefore, it becomes a high impedance and acts to decrease the gain of both amplifiers A6 and A7. Conversely, if the output of the AGC section 54 as it appears at pin 14 of amplifier A7 decreases in amplitude, a smaller DC potential will exist across electrolytic capacitor C13. Accordingly, FET 1 will move further away from its cutoff region and the value of the impedance between its source and drain will be reduced thereby effectively increasing the gain of AGC circuit 54. The action of the circuit is such as to hold the output signal appearing at pin 14 of amplifier A7 at a constant level of approximately 7 volts. The signal appearing at the output of AGC section 54 is negative going under all circumstances.

The output of the initial signal processing unit 34 (See output signal "A" in FIG. 5A) is applied through a Texas Instrument type 1N914 diode D5 and a coupling 100 microfarads electrolytic capacitor C14 to pin 3 of amplifier A8 (See input signal "A" in FIG. 5B). Threshold detecting circuit 56 essentially comprises amplifier A8 and a diode clipping circuit which includes diode D5 and a voltage divider comprising a 62 K ohm resistor R3 in series to round through a 39 K ohm resistor R24. Resistor R23 is connected to a negative 9 volt source. Accordingly, no signal appears at the junction of resistors R23 and R24 until it exceeds a negative 4 volt value. It is then coupled to amplifying stage A8. The input to pin 3 of amplifier A8 includes a 100 K ohm resistor R25 to ground connected to the diode clipping circuit by means of coupling capacitor C14 in the manner previously described. The signal is amplified in circuit A8 with a gain of 10. The gain of amplifier A8 is determined by a 100 K ohm resistor R27 connected between pin 6 and pin 2 and a 10 K ohm resistor 26 connected between pin 2 and ground. Amplifier A8 comprises a National Semiconductor type 741 integrated circuit. Diode D6 which is connected to pin 6 of amplifier A8 is a Texas Instrument type 1N914 diode and is there for the purpose of protecting subsequent stages.

The output of amplifier A8 is connected via a 1 microfarad capacitor C15 to the input of monostable stage 58. Monostable stage 58 essentially comprises gates A9 and A10 and associated coupling capacitors and resistances. Gates A9 and A10 together with gates A11 and A12 are all part of the same RCA type CD 4011 integrated circuit. A one megohm resistor R28 connects pin 1 of gate A9 to ground. The output pin 3 of gate A9 is connected via a 0.1 microfarad coupling capacitor C16 to the input of gate A10. A 1.5 megohm resistor R29 connects the input of gate stage A10 to ground. The output pin 4 of gate A10 is connected to the second input terminal pin 2 of gate A9. Each time a QRS spike complex is introduced at pin 1 of gate A9, the monostable circuit will produce a uniform 9 volt negative going square wave having a duration of approximately 100 milliseconds duration.

The standardized output signal produced by monostable 58 is introduced as an input signal to pin 1 of counter CR1. Eight beat counter CR1 preferably comprises an RCA type CD 4024 circuit. The counter produces a high level signal at its output pin 6 when eight pulses have been counted.

The output (See output signal "B" in FIG. 5B) of the eight beat counter CR1 is connected to the input of timing pulse generator 62. As previously described the timing pulse generator 62 produces two narrow control pulses each 10 milliseconds wide and having the leading edge of the second pulse coincident with the trailing edge of the first pulse. The operation of the timing pulse generator 62 may be understood from the following description. When pin 6 of the eight beat counter CR1 goes high at the end of the eighth heart beat (Signal "B"), that potential is applied through 100 K ohm resistor R30 to the base of a National Semiconductor type 2N4124 transistor T1. A 0.2 microfarad capacitor C17 connected between the base and collector of transistor T1 introduces a time delay. A time delay is introduced because capacitor C17 prevents the collector of transistor T1 from falling in potential instantaneously. The time delay is also partially controlled by the presence of 100 K ohm resistor R31 connected between the collector of T1 and circuit ground. The output of time delay transistor T1 is connected to pin 2 of gate A11. Gates A11 and A12 comprise parts of a second monostable circuit which is not activated for a time period that is determined primarily by resistors R30, R31 and delay capacitor C17. The second monostable circuit includes a 0.1 microfarad coupling capacitor C18 connecting the output of gate A11 to one of the inputs of gate A12. The input of gate A12 is connected to the center junction of a voltage dividing resistor circuit comprising a 6.8 megohm resistor R32 and a 1.8 megohm resistor R33. The output pin 11 of gate A12 is connected to an input pin 9 of gate A11. After approximately 10 milliseconds have passed, the second monostable circuit is triggered and an output pulse (See signal "C" in FIG. 5B) appears at pin 11. The output pulse "C" at pin 11 is coupled back to pin 2 of the eight beat counter CR1 so as to reset the eight beat counter to the zero state. The pulse "C" produced by the second monostable circuit continues for approximately 10 milliseconds after initiation.

It can therefore be seen from the foregoing that the eight beat counter circuit produces a first 10 millisecond pulse "B" and that the first 10 millisecond pulse is employed to trigger a second monostable circuit which produces a second pulse "C" whose leading edge is coincident with the trailing edge of the first pulse "B" produced by the eight beat counter circuit. In short, at the end of each eight heart beat period, two relatively narrow pulses are produced in rapid sequence.

A third and final stage 38 is connected to the output of the QRS recognition circuit 36. The first part of the third stage 38 comprises a ramp generator 64 which produces a ramp that increases at a linear rate with respect to time. The ramp generator 64 essentially comprises a Miller type integrating circuit including amplifier section A13 and a feedback integrating capacitor C21 connected between output pin 6 and input pin 2 of amplifier A13. Amplifier A13 comprises a National Semiconductor type LM 308 operational amplifier and feedback capacitor C21 comprises a 1.5 microfarad capacitor. Amplifier A13 is connected to a source of constant current (See output signal "D" in FIG. 5B) which allows the integrating capacitor C21 to charge up at a relatively linear rate. The current source includes a 15 K ohm resistor R34 in series with a 6.5 volt Zener diode ZD1. The junction of R34 and ZD1 is connected through a 620 K ohm resistor R35 to a 100 K ohm variable potentiometer R34 and a 360 K ohm fixed resistor R38 to the second pin of amplifier A13. A 22 K ohm resistor R36 and a 100 microfarad capacitor C19 are connected in parallel between the junction of resistors R35 and R37 and ground. The integrating time constant of the ramp generator 64 is determined by integrating capacitor C21, potentiometer R37 and fixed resistor R38. A Siliconix type 2N4220 field effect transistor FET2 is connected across integrating capacitor C21 and acts as a switch. The gate of FET2 is connected through a 1 megohm resistor R39 to the output (Signal "C") of the timing pulse generator 62 which originates at the output of gate A11. The gate of FET2 is also connected to ground through a 390 microfarad capacitor C20. When the second timing pulse "C" arrives at the gate of FET2, the field effect transistor conducts and the ramp generator is reset to zero.

Output pin 6 of amplifier A13 is connected through a 2.2 K ohm resistor R40 to input pin 3 of amplifier A14. This comprises the first stage of the sample-and-hold circuit 66. Amplifier A14 is an RCA type CA 3080 operational amplifier. Output pin 6 of operational amplifier A14 is connected to a 0.33 microfarad holding capacitor C23, the other side of which is connected to circuit ground. Pin 6 is also connected to the gate of an insulated gate field effect transistor FET3. FET3 is preferably a type 3N128 buffering insulating field effect transitor. (IGFET) The source of FET3 is connected through a 29 K ohm resistor R43 to a negative 9 volt potential. The drain of FET3 is connected to a positive 9 volt potential. The source of FET3 is also connected via the parallel combination of a 22 K ohm resistor R42 and a 120 picofarad capacitor C24 to a second input pin 2 of amplifier A14. Pin 5 of operational amplifier A14 is connected through the parallel combination of a 18 K ohm resistor R41 and a 270 microfarad capacitor C22 to the output pin 9 of eight beat counter CR1. Just before the second control pulse "C" from timing pulse generator 62 resets ramp generator 64, the first control pulse "B" from the eight beat counter CR1 turns on the operational amplifier A14 through elements R41 and C22. This causes holding capacitor C23 to charge to a voltage proportional to the instantaneous voltage in the ramp generator 64 just prior to the ramp generator 64 being reset. The voltage on capacitor C23 does not readily leak away due to the high impedance of insulated gate field effect transistor FET3. Accordingly, it is clear that the timing pulses "B" and "C" perform two functions. First of all, timing pulse "B" activates sample-and-hold amplifier 66 so that capacitor C23 can store the instantaneous value of the ramp generator 64. Secondly, the second timing pulse "C" resets the ramp generator 64 to the ground state in order to begin a new counting cycle. It is also clear that the potential at the source of FET3 is proportional to the time that it takes eight heart beats to occur.

The last major portion of the electronic package 16 is the ratiometric analog-to-digital converter 68. This circuit employs a variation of a technique commonly known as "Dual Slope" analog-to-digital conversion. The operation of circuit 68 will be more fully understood by a quick general review of the theory of "Dual Slope" analog-to-digital conversion. In theory an integrator is normally held in the negative saturated state. A reference potential is applied to the input of the integrator to cause the integrator to ramp upward at a constant rate. A comparator then examines the output of the integrator. When it crosses over zero it enables a clock generator which is connected to a three decade counter. The integrator is allowed to ramp up for 1,000 counts. At the end of the 1,000 counts, the potential the inverse of which is to be measured is now applied to the integrator. At the end of 1,000 counts the three decade counter naturally reads 000. The potential whose inverse is to be read is applied with the opposite polarity with respect to the reference signal. The integrator then ramps downwards and the counter is shut off when the integrator once again crosses over the zero point. The result is that the number remaining in the three decade counter is proportional to the inverse of the input potential. This value is independent of the clock frequency and also independent of the value of the RC time constant associated with the integrator. The foregoing explanation should make the operation of the specific circuit elements easier to understand.

The ratiometric analog-to-digital converter 68 described in FIG. 5C operates in the following manner. The first timing pulse "B" clears counters CR2 and CR3. The next timing pulse "C" enters pin 6 of bistable flip flop FF1. FF1 is an RCA type CD 4013 integrated circuit. Second timing pulse "C" causes pin 1 of FF1 to go high which in turn causes transistor T2 to conduct and it in turn turns on field effect transistor FET4. T2 is a National Semiconductor type 2N4124 transistor and FET4 is a Siliconix type 2N2844 field effect transistor. Pin 1 of FF1 is connected via a 22 K ohm resistor R62 to the base of transistor T2. The base of transistor T2 is also connected through a 100 K ohm resistor R47 to a plus 9 voltage source. The emitter of T2 is connected to ground and the collector of T2 is connected through a 100 K ohm resistor R 46 to a plus 9 volt source. One side of FET4 is connected through a 1 megohm resistor R45 to the reference DC potential "D" supplied by zener diode ZD1 and stored on capacitor C19. (See FIG. 5B) When FET4 is conducting the DC potential "D" is applied to pin 2 of amplifier A15. Amplifier A15 is normally in the negative saturated state and comprises a National Semiconductor type LM 308 operational amplifier. Pin 3 of amplifier A15 is connected through a 1 megohm resistor R48 to ground. Output pin 4 of amplifier A15 is connected through a 0.0039 microfarad integrating capacitor C25 to input pin 2. Therefore, when the reference DC potential "D" is applied through FET4 to input pin 2 of amplifier A15, the Miller integrator begins to ramp upward. The output of the integrator is applied through a 1 K ohm resistor R49 to input pin 5 of operational amplifier A16. Operational amplifier A16 comprises a Fairchild Semiconductor 715 operational amplifier which acts as a high speed comparator. A 10 picofarad capacitor C26 is connected between pins 2 and 14 of amplifier A16. Pin 13 is connected to a plus 9 volt voltage source. Pin 10 is connected to a minus 9 volt voltage source. Output pin 11 is connected to a 4.7 megohm resistor R51 to input pin 4. Input pin 4 is also connected through a 1 K ohm resistor R50 to ground.

Output pin 11 of amplifier A16 is connected to the 100 K ohm resistor R52 which in turn is connected to the base of transistor T3. Transistor T3 comprises a National Semiconductor type 2N4124 transistor and acts as a voltage shifting element. The base of transistor T3 is connected through a 10 K ohm resistor R54 to the emitter of transistor T3. The emitter in turn is connected directly to a minus 9 volt voltage source. The collector of transistor T3 is connected through a 100 K ohm resistor R53 to ground and also to input pin 9 of the first stage of counter circuit CR2. Counter circuit CR2 comprises a Motorola type MC 14518 counter.

Pin 9 of CR2 is the enable input for the counter. Pin 10 of CR2 is connected to a 10 kilohertz clock generator which includes gates A17 and A18. A17 and A18 are each one quarter of an RCA type CD 4001 integrated circuit. Output pin 10 of gate A17 is connected to input pins 12 and 13 of gate A18. Output pin 11 of gate A18 is connected through a 0.001 microfarad capacitor C28 to a 100 K ohm resistor R57 back to the input pins 8 and 9 of gate A17. A 39 K ohm resistor R58 also connects the output pin 10 of gate A17 to the junction of resistor R57 and capacitor C28. Output pin 11 of gate A18 is connected to input pin 10 of counter CR2. The frequency of the 10 kilohertz clock is determined primarily by capacitor C28 and resistor R58. The 10 kilohertz clock produces a series of square waves which are fed into counter CR2. As the integrator formed by amplifier A15 and capacitor C25 ramps upward and crosses zero, the counter CR2 is enabled and the 10 kilohertz clock is read into counter CR2. The three decade counter comprises two counter circuits, namely CR2 and CR3. Both CR2 and CR3 are Motorola type MC 14518 counters. CR2 feeds into CR3 and accordingly, CR2 records the least significant bit and CR3 records the most significant bit. The most significant bit, that is the bit associated with the 1,000th count of the three decade counter, appears at pin 14 of CR3. Pin 14 of CR3 is also connected via the parallel combination of a 100 K ohm resistor R56 and a 220 microfarad capacitor C27 to the base of transistor T4. Transistor T4 is a National Semiconductor type 2N4124 transistor whose emitter is connected to a minus 9 volt source and whose collector is connected through a 100 K ohm resistor R55 to ground. The collector of T4 is also connected to a second input of FF1. The signal applied to the second input will cause FF1 to change stage. Accordingly, the advent of a 1,000 count appearing at pin 14 of CR3 will cause FF1 to change state. Pin 1 of FF1, which was previously high now drops to low and cuts off FET4. As pin 1 of FF1 goes low, pin 2 of FF1 goes high. Pin 2 of FF1 is connected to the gate of field effect transistor FET5. One control lead of FET5 is connected through a 1 megohm resistor R44 to the potential stored in the sample-and-hold circuit 66. This signal is derived from the potential "E" appearing at the source of FET3 (See FIG. 5B). The sample-and-hold signal is then applied to the Miller integrator A15 with a polarity opposite to that of the reference signal. The integrator now ramps downwards. When the integrator crosses the zero point the potential at pin 9 of CR2 changes, the 10 kilohertz clock becomes disabled and counter CR2 and CR3 hold a count which is proportional to the inverse of the input potential.

The outputs of CR2 and CR3 are connected to decoding circuits DEC1, DEC2, and DEC3. The decoding circuits convert the output of counters CR2 and CR3 into binary coded decimals. The output of the counters must be decoded so as to drive the seven segments (a, b, c, d, e, f, g) associated with each digit of a conventional liquid crystal display. The manner in which the binary connections a through g are made is entirely conventional and well known to those of ordinary skill in the art. Also conventional is the use of a 60 hertz clock or the like as an input to the decoding circuitry. In this case the 60 hertz clock is connected to pin 6 of DEC1. The 60 hertz clock includes gates A19 and A20 which comprise the other one quarter of an RCA integrated circuit CD 4001. Output pin 3 of gate A19 is connected to input pins 5 and 6 of gate 20. Output pin 4 of gate 20 is connected via a 1 microfarad capacitor C29 and a 1 megohm resistor R54 to input pins 1 and 2 of gate A19. The junction of R59 and C29 is connected through a 68 K ohm resistor R60 and the parallel combination of a 27 K ohm resistor R51 and a diode D7 to output pin 3 of gate A19.

There are other modifications of the above described preferred embodiment which may be desirable under certain circumstances. One possible modification might be to employ a DC to DC converter which would allow operation of the cardiotachometer from a single battery. That is, the DC to DC converter would convert the 9 volt potential arising from a single battery to the necessary +/−9 volts required by the electronic circuitry. Additionally, even though the circuitry described consumes a very small amount of power, it would be desirable to cut the power consumption even more. Liquid crystals are especially attractive because of their power consumption. However, the present integrated circuits do consume an appreciable amount of power and it may be desirable to substitute other integrated circuits for the ones presently used in order to further minimize power consumption.

Another area which may entail some modification is the possible addition of circuitry which would allow for leading zero blanking. With the present circuitry any heart rate less than 100 beats per minute will be displayed with a zero in the most significant position followed by 2 digits. For example, 72 beats per minute is now displayed as 072. It would probably be less confusing to illustrate this number as simply 72.

Finally, the unit might preferably be converted to cover an average of other multiples of 2 heart beats rather than eight heart beats. This would of course, entail the changing of the counter from a eight beat counter to an N beat counter, where N is a multiple of 2, and would further involve the changing of the time constant associated with the ramp generator. An eight heart beat time segment was chosen so as to minimize heart beat irregularities and also to give the user an opportunity to view the display. For example, if the period between consecutive heart beats were counted, then the heart rate display for an individual with a heart beat of 70 bpm would change at the rate of more than once per second. This would, of course, be very difficult to display and read and is a major advantage of the present device.

The following is a parts list of the major elements incorporated into the electronic circuitry.

| INTEGRATED CIRCUITS | |
|---|---|
| A1 | Burr-Brown Type 3660J |
| A2 | National Semiconductor LM 747 |
| A3 | " |
| A4,A5,A6,A7 | National Semiconductor LM 324 |
| A8 | National Semiconductor LM 741 |
| A9,A10,A11,A12 | RCA CD 4011 |
| A13 | National Semiconductor LM 308 |
| A14 | RCA CA 3080 |
| A15 | National Semiconductor LM 308 |
| A16 | Fairchild Semiconductor 715 |
| A17,A18,A19,A20 | RCA CD 4001 |
| CR1 | RCA CD 4024 |
| CR2, CR3 | Motorola MC 14518 |
| DEC1, DEC2, DEC3 | RCA CD 4055 |
| FF1 | RCA CD 4013 |
| TRANSISTORS | |
| FET1 | Motorola HEP 801 |
| FET2, FET5 | Siliconix 2N4220 |
| FET3 | Fairchild Semiconductor 3N128 |
| FET4 | Siliconix 2N2844 |
| T1, T2, T3, T4 | National Semiconductor 2N4124 |

| | DIODES | |
|---|---|---|
| D1–D4 | Hewlett-Packard 5082-2835 | |
| D5–D7 | Texas Instruments 1N 914 | |

RESISTORS (All resistors are Ohmite "Little Devils" ¼ watt, 5% tolerance unless otherwise specified).

| | |
|---|---|
| R1 | 10 megohm |
| R2 | 100 ohm |
| R3 | 100 K ohm |
| R4 | 51 K ohm |
| R5 | 51 K ohm |
| R6 | 110 K ohm |
| R7 | 110 K ohm |
| R8 | 33 K ohm |
| R9 | 39 K ohm |
| R10 | 10 K ohm |
| R11 | 10 K ohm |
| R12 | 10 K ohm |
| R13 | 1 K ohm |
| R14 | 4.7 K ohm |
| R15 | 10 K ohm |
| R16 | 10 K ohm |
| R17 | 68 K ohm |
| R18 | 220 K ohm |
| R19 | 68 K ohm |
| R20 | 47 K ohm |
| R21 | 150 K ohm |
| R22 | 1 megohm |
| R23 | 62 K ohm |
| R24 | 39 K ohm |
| R25 | 100 K ohm |
| R26 | 10 K ohm |
| R27 | 100 K ohm |
| R28 | 1 megohm |
| R29 | 1.5 megohm |
| R30 | 100 K ohm |
| R31 | 100 K ohm |
| R32 | 6.8 megohm |
| R33 | 1.8 megohm |
| R34 | 15 K ohm |
| R35 | 620 K ohm |
| R36 | 22 K ohm |
| R38 | 360 K ohm |
| R39 | 1 megohm |
| R40 | 2.2 K ohm |
| R41 | 18 K ohm |
| R42 | 22 K ohm |
| R43 | 29 K ohm |
| R44 | 1 megohm |
| R45 | 1 megohm |
| R46 | 10 K ohm |
| R47 | 100 K ohm |
| R48 | 1 megohm |
| R49 | 1 K ohm |
| R50 | 1 K ohm |
| R51 | 4.7 megohm |
| R52 | 100 K ohm |
| R53 | 10 K ohm |
| R54 | 10 K ohm |
| R55 | 10 K ohm |
| R56 | 100 K ohm |
| R57 | 100 K ohm |
| R58 | 39 K ohm |
| R59 | 1 megohm |
| R60 | 68 K ohm |
| R61 | 27 K ohm |
| R62 | 22 K ohm |

POTENTIOMETERS

| | |
|---|---|
| R37 | Clarostat 100 K Ohm, 10 turn Cermet precision potentiometer |

CAPACITORS (Ceramic Disc capacitors - all are Centralab Hi K Kaps)

| | |
|---|---|
| C1 | 1 microfarad |
| C2 | 150 microfarad electrolytic |
| C3 | .15 microfarad |
| C4 | .15 microfarad |
| C6 | .15 microfarad |
| C7 | 0.47 microfarad |
| C8 | 50 microfarad electrolytic |
| C9 | .05 microfarad |
| C10 | 1 microfarad |
| C11 | .005 microfarad |
| C12 | 0.1 microfarad |
| C13 | 100 microfarad electrolytic |
| C14 | 10 microfarad electrolytic |
| C15 | 1 microfarad |
| C16 | .1 microfarad |
| C17 | 0.2 microfarad |
| C18 | .01 microfarad |
| C19 | 100 microfarad electrolytic |
| C20 | 390 micro microfarad |
| C21 | 1.5 microfarad mylar |
| C22 | 270 micro microfarad |
| C23 | .33 microfarad |
| C24 | 120 picofarad |
| C25 | .0039 microfarad |
| C26 | 10 picofarad |
| C28 | .001 microfarad |
| C29 | .1 microfarad |

The four 1 microfarad capacitors are all Erie High Capacity Ceramic capacitors. The 1.5 mircrofarad capacitor is a mylar capacitor manufactured by Midwec Type 7X. The four 0.15 microfarad 50% mylar capacitors were manufactured by Callins as was the 0.33 microfarad mylar capacitor. All electrolytic capacitors are Sprague "Atom" Aluminum Electrolytic.

While the invention has been described in terms of its preferred embodiment and the best mode of its use, it will be understood by those of skill in the art that various modifications may be made in the structure of the device or the juxtaposition of the components without departing from the spirit and scope of the invention.

We claim:

1. A cardiotachometer apparatus comprising:
    a pick-up means for picking up electrical signals from heart beats;
    an initial signal processing means having an input connected to said pick-up means and an output, said initial signal processing means including an amplifier means therein;
    a signal recognizing means having an input connected to the output of said initial signal processing means, said signal recognizing means including a heart beat counter means for counting said heart beats and producing an output once for every Nth heart beat, N being equal to or greater than 2, said output occuring at intervals T apart;
    a reciprocal generating means for producing an output directly proportional to 1/T, said reciprocal generating means including:
        a ramp generator having an input and an output, the input of said ramp generator being connected to the output of said signal recognizing means;
        a sample-and-hold means having at least two inputs and one output, one of said sample-and-hold inputs being connected to the output of said ramp generator and one of said other inputs of said sample-and-hold generator being connected to the output of said signal recognizing means; and,
        a ratiometric dual/slope analog-to-digital conversion means having at least two inputs and one output, at least one of said inputs to said ratiometric dual/slope analog-to-digital conversion means being connected to the output of said sample-and-hold means and at least one of the other of said inputs of said ratiometric dual/slope analog-to-digital conversion means being connected to the output of said signal recognizing means; and, a display means for producing a visual output, said display means being connected to said reciprocal generating means, the output of said display means being directly proportional to the heart beat rate between outputs of said counter means.

2. The apparatus of claim 1 further including:
an automatic polarity selecting circuit means included in said initial signal processing means for producing an output of specified polarity in response to an input of either positive or negative polarity.

3. The apparatus of claim 1 further including:
a common mode rejection means incorporated in said initial signal processing means.

4. The apparatus of claim 3 wherein said common mode rejection means comprises a differential amplifier.

5. The apparatus of claim 4 wherein said pick-up means comprises a three electrode system.

6. The apparatus of claim 1 wherein said initial signal processing means comprises:
a differential amplifier having an input and an output, the input of said differential amplifier being connected to said pick-up means;
a bandpass filter having an input and an output, the input of said bandpass filter being connected to the output of said differential amplifier;
an automatic polarity selector having an input and an output, the input of said automatic polarity selector being connected to the output of said bandpass filter; and,
an automatic gain control amplifier having an input and an output, the input of said automatic gain control amplifier being connected to the output of said automatic polarity selector.

7. The apparatus of claim 1 wherein said signal recognizing means comprises:
a threshhold detector having an input and an output, the input of said threshhold detector being connected to the output of said initial signal processing means;
a monostable circuit having an input and an output, the input of said monostable circuit being connected to the output of said threshhold detector;
an Nth beat counter means having an input and an output, the input of said Nth beat counter means being connected to the output of said monostable circuit; and,
a timing pulse generator having an input and an output, the input of said timing pulse generator being connected to the output of said Nth beat counter.

8. The apparatus of claim 6 wherein said signal recognizing means comprises:
a threshhold detector having an input and an output, the input of said threshhold detector being connected to the output of said initial signal processing means;
a monostable circuit having an input and an output, the input of said monostable circuit being connected to the output of said threshhold detector;
an Nth beat counter means having an input and an output, the input of said Nth beat counter means being connected to the output of said monostable circuit; and,
a timing pulse generator having an input and an output, the input of said timing pulse generator being connected to the output of said Nth beat counter.

9. The apparatus of claim 8 wherein said display means comprises:
a liquid crystal display.

10. The apparatus of claim 9 wherein said Nth beat counter produces one output pulse for every eight input pulses.

11. The apparatus of claim 1 wherein said dual/slope analog-to-digital conversion means comprises:
a counter means;
a clock means connected to said counter means;
a first means for activating said counter means until it reaches a predetermined count;
a switch means connected to said counter means and activated by said counter means when said counter means reaches said predetermined count; and,
a second means connected to said switch means for reactivating said counter means after said predetermined count has been made.

12. The apparatus of claim 11 further comprising:
an integrator means having the input thereof connected to said first and second means and the output thereof connected to said counter means.

13. The apparatus of claim 12 wherein said switch means comprises a flip-flop circuit.

14. The apparatus of claim 13 further comprising:
a high speed comparator means and a voltage level shifting means connected between the output of said integrator means and the input of said counter means.

15. The apparatus of claim 14 wherein said flip-flop means includes a first and a second output terminals, said first and second output terminals being the inverse of each other; and,
wherein said first and said second means includes field effect transistor switch means therein having the input gates thereof respectively connected to the first and second output terminals of said flip-flop.

* * * * *